US00PP34746P2

(12) United States Plant Patent
Sharoni et al.

(10) Patent No.: US PP34,746 P2
(45) **Date of Patent: *Nov. 15, 2022**

(54) ***PORTULACA* PLANT NAMED 'DPORMPZGL'**

(50) Latin Name: *Portulaca oleracea*
Varietal Denomination: DPORMPZGL

(71) Applicant: Danziger 'DAN' Flower Farm, Beit Dagan (IL)

(72) Inventors: Pazit Sharoni, Beit Dagan (IL); Amir Zuker, Beit Dagan (IL); Gavriel Danziger, Beit Dagan (IL)

(73) Assignee: Danziger "Dan" Flower Farm

( * ) Notice: Subject to any disclaimer, the term of this patent is extended or adjusted under 35 U.S.C. 154(b) by 0 days.

This patent is subject to a terminal disclaimer.

(21) Appl. No.: 17/571,070

(22) Filed: Jan. 7, 2022

Related U.S. Application Data

(63) Continuation of application No. 17/246,084, filed on Apr. 30, 2021.

(51) Int. Cl.
*A01H 5/02* (2018.01)
*A01H 6/00* (2018.01)

(52) U.S. Cl.
USPC ..... Plt./471
CPC ..... *A01H 6/00* (2018.05)

(58) Field of Classification Search
USPC ..... Plt./471; 800/298, 295, 260
CPC ..... A01H 6/00
See application file for complete search history.

(56) References Cited

U.S. PATENT DOCUMENTS 17,571,070 * 4/2021 Sharoni et al. ..... A01H 6/00
800/298

* cited by examiner

*Primary Examiner* — Anne Marie Grunberg
(74) *Attorney, Agent, or Firm* — Cassandra Bright

(57) ABSTRACT

A new and distinct cultivar of *Portulaca* plant named 'DPORMPZGL' is disclosed, characterized by large, vivid yellow flowers, dark green foliage, and a semi-trailing habit. The new variety is a *Portulaca*, typically produced as an ornamental plant.

2 Drawing Sheets

Figure 1:
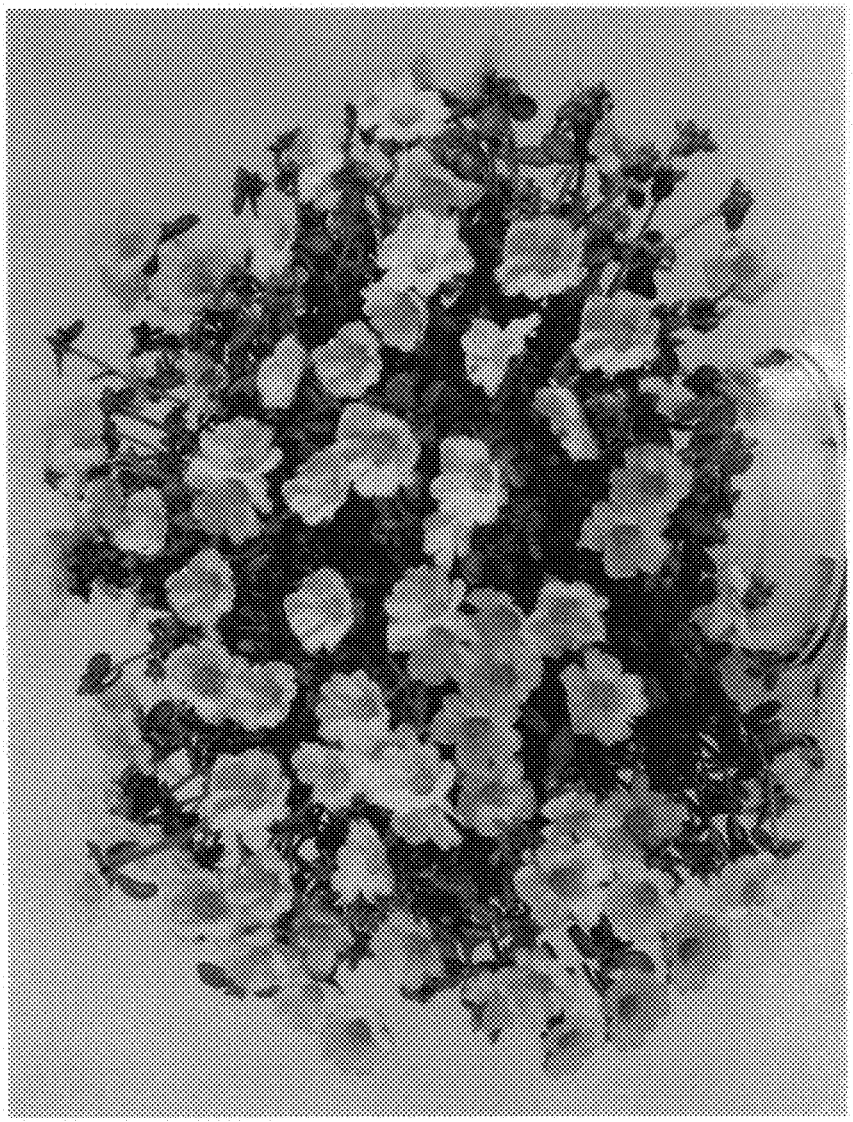

Latin name of the genus and species: *Portulaca oleracea*.
Variety denomination: 'DPORMPZGL'.

BACKGROUND OF THE INVENTION

The new *Portulaca* cultivar is a product of a planned breeding program conducted by the inventors, Pazit Sharoni, Amir Zuker and Gavriel Danziger in Moshav Mishmar Hashiva, Israel. The objective of the breeding program was to produce useful new *Portulaca* varieties for ornamental horticultural production. The open-pollination resulting in this new variety was made during 2016.

The seed parent is the unpatented, propriety variety referred to as *Portulaca* 'PT-16-1356'. The pollen parent is unidentified. The new variety was discovered in July of 2017 by the inventor in a group of seedlings resulting from the 2016 open pollination, in a greenhouse in Moshav Mishmar Hashiva, Israel. After selection of the new variety, extensive confidential testing has been performed to determine and define the desirable characteristics of the new variety.

Asexual propagation of *Portulaca* 'DPORMPZGL' was performed by vegetative basal cuttings during September of 2017 at a research greenhouse in Moshav Mishmar Hashiva, Israel.

SUMMARY OF THE INVENTION

The cultivar 'DPORMPZGL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPORMPZGL'. These characteristics in combination distinguish 'DPORMPZGL' as a new and distinct *Portulaca* cultivar:

1. Controlled, semi-trailing habit.
2. Large flowers.
3. Vivid yellow flower color.
4. Dark green foliage.

PARENT COMPARISON

Plants of 'DPORMPZGL' are similar in some horticultural characteristics to the seed parent. The new variety, however, differs in the following:

1. Flowers of the new variety are yellow; flowers of the seed parent are dark orange with a large yellow center.
2. Flowers of the new variety are more open and nearly flat; flowers of the seed parent are more conical to funnel-shaped.
3. Foliage of the new variety is darker than foliage of the seed parent.

Comparison with the pollen parent is unavailable, as this variety resulted from an open pollination.

COMMERCIAL COMPARISONS

Plants of 'DPORMPZGL' are similar in some horticultural characteristics to the variety *Portulaca* 'Nano Yellow', unpatented. The new variety, however, differs in the following:

1. This comparator has a more compact and dense habit than 'DPORMPZGL'.
2. The flowers color of this comparator is brighter yellow than flowers of 'DPORMPZGL'.
3. Foliage color of this comparator is brighter green than foliage of 'DPORMPZGL'.
4. Foliage color of this comparator is larger than foliage of 'DPORMPZGL'.

Plants of 'DPORMPZGL' are similar in some horticultural characteristics to the variety *Portulaca* 'Cupcake Yellow Chrome', unpatented. The new variety, however, differs in the following:

1. The plant habit of 'DPORMPZGL' is semi-trailing; the plant habit of this comparator is trailing.
2. 'DPORMPZGL' produces larger flowers than this comparator.
3. 'DPORMPZGL' produces yellow flowers; this comparator produces yellow flowers with orange venation.

BRIEF DESCRIPTION OF THE PHOTOGRAPHS

The accompanying photograph in FIG. 1 illustrates in full color a typical plant of 'DPORMPZGL' at about 8 weeks of age, grown in a 13 cm pot.

Figure 2:
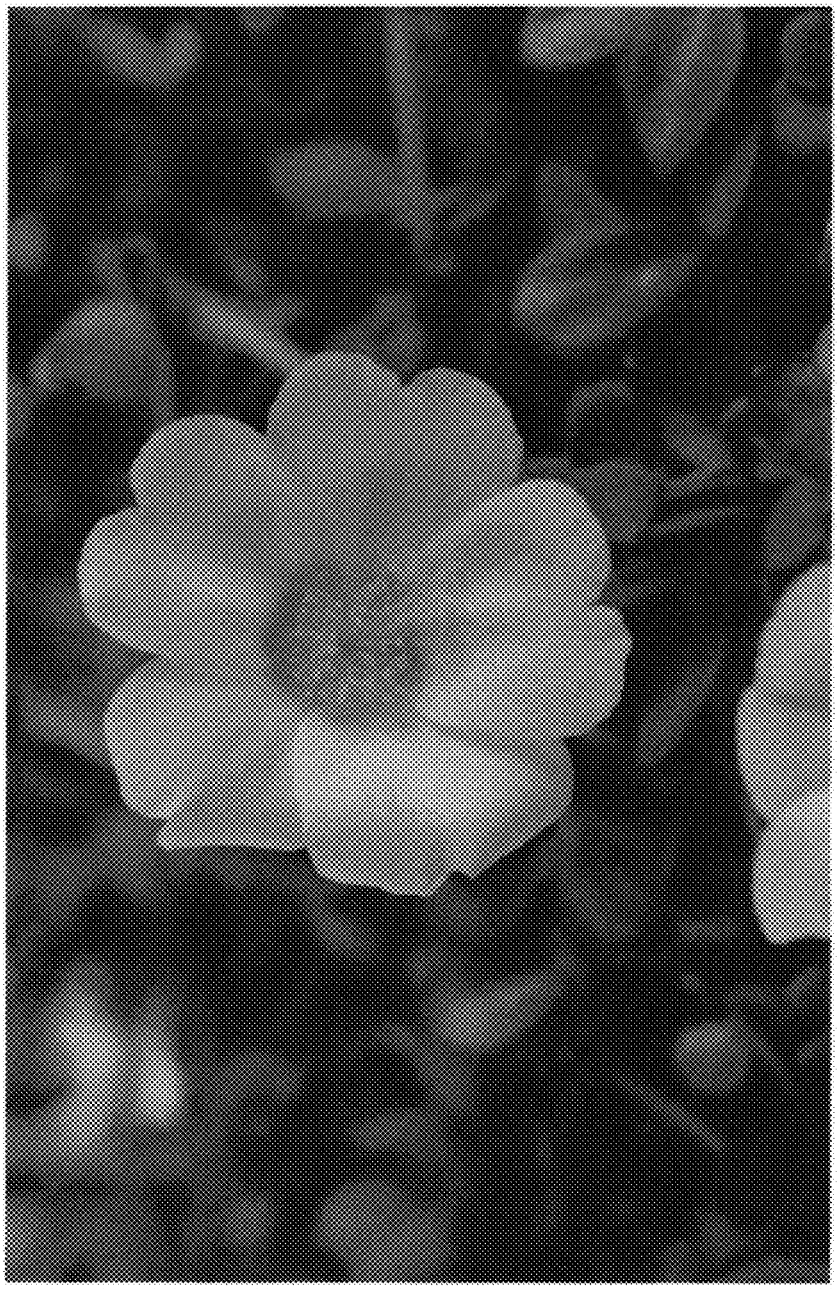

FIG. 2 illustrates a closer view of a typical flower of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DPORMPZGL' plants grown outdoors in Moshav Mishmar Hashiva, Israel, under natural lighting. Measurements were taken during Spring. The growing temperature ranged from approximately 24° C. to 38° C. during the days, 12° C. to 26° C. during the nights. Measurements and numerical values represent averages of typical plant types.

Botanical classification: *Portulaca oleracea* 'DPORMPZGL'.

PROPAGATION

Time to initiate rooting: Vegetative cuttings.
Root description: 10 to 12 days at approximately 24° C.
Root description: Fine, fibrous; close to Yellow-White 158B in color, freely branching.

PLANT

Growth habit: Semi-trailing.
Pot size of plant described: 13 cm.
Height: About 16 cm.
Plant spread: About 28 cm radius.
Growth rate: Medium vigor.
Branching characteristics:
Length of lateral branches: 26 cm.
Diameter of lateral branches: 0.6 cm.
Quantity of lateral branches: About 9 per main stem.
Characteristics of primary lateral branches:
*Diameter.*—About 0.35 to 0.4 cm.
*Color.*—Tip near RHS Yellow-Green 144B; base near RHS Red-Purple 59B (Anthocyanin coloration).
*Texture.*—Glabrous.
*Strength.*—Moderately strong.
Internode length: 1.8 to 3 cm.
Age of plant described: Approximately 98 days from a rooted cutting.

FOLIAGE

Leaf:
*Arrangement.*—Alternate, simple.
*Quantity.*—Approximately 15 per branch.
*Average length.*—2.5 cm.
*Average width.*—1.2 to 1.6 cm.
*Pubescence.*—Glabrous, succulent.
*Shape.*—Obovate.
*Apex.*—Rounded, slightly mucronate.
*Base.*—Cuneate.
*Margin.*—Entire.
*Texture.*—Smooth, both sides.
*Aspect.*—About 45-80°.
*Color.*—Young, Upper side: Near RHS Green 137B. Young, Under side: Near RHS Green 138A. Mature, Upper side: Near RHS Green N137A. Mature, Under side: Near RHS Green 138A.
*Venation.*—Indistinguishable from leaf blade.
Petiole:
*Length.*—About 1.2 mm.
*Diameter.*—About 1 mm.
*Color.*—Near RHS Yellow-Green 144B.
*Texture.*—Smooth, glabrous.

FLOWER

Natural flowering season: Spring to Fall.
Days to flowering from rooted cutting: About 4 weeks to the first flowers.
Inflorescence and flower type and habit: Single flower, abundant flowering.
Rate of flower opening: About 3 days from bud to fully opened flower.
Flower longevity on plant: About 1 to 2 days.
Persistent or self-cleaning: Self-cleaning.
Bud:
*Buds per lateral stem.*—15 to 20.
*Shape.*—Ovoid.
*Length.*—1 to 1.2 cm.
*Diameter.*—0.7 cm.
*Color.*—Near RHS Yellow-Green 144B; tip near RHS Green 143B.
Flower size:
*Diameter.*—About 5 cm.
*Depth.*—About 2 cm.
Corolla/petals:
*Arrangement.*—5 petals merged/fused at the base.
*Length.*—2.5 cm.
*Width.*—2.1 to 2.3 cm.
*Quantity.*—5 petals.
*Texture.*—Smooth, glabrous.
*Apex.*—Emarginate to retuse.
*Shape.*—Obovate with a cuneate base.
*Margin.*—Entire.

*Aspect*.—Mostly flat, upper margin slightly rolled down.

*Color*.—When Opening, Upper Surface: RHS Yellow 9A. When Opening, Lower Surface: RHS Yellow 9B. Fully Opened, Upper Surface: RHS Yellow 9A. Fully Opened, Lower Surface RHS Yellow 9B.

Calyx/sepals:

*Quantity per flower*.—2.

*Shape*.—Fused into a tubular calyx. Pointed apex.

*Length*.—0.9 to 1 cm.

*Width*.—0.8 cm.

*Apex*.—Acute.

*Base*.—Fused.

*Margin*.—Entire.

*Texture*.—Glabrous.

*Color*.—Upper Surface: RHS Yellow-Green 144A. Lower Surface: Near RHS Yellow-Green 144B.

Peduncles: None.

Fragrance: None.

REPRODUCTIVE ORGANS

Androecium:

Stamens:

*Number*.—Many, about 60.

*Filament length*.—Approximately 0.5 cm to 0.6 cm.

Anthers:

*Shape*.—Oval.

*Length*.—About 0.6 mm.

*Color*.—Near RHS Yellow-Orange 14A.

*Pollen*.—Color: RHS Yellow-Orange 17A. Quantity: Abundant.

Gynoecium:

Pistil:

*Number*.—1.

*Length*.—1.1 cm.

*Style*.—Length: 0.7 cm. Color: Near RHS Yellow 9B.

*Stigma*.—Shape: Six branched stigma. Color: Near RHS Yellow 9A. Ovary Color: Near RHS Yellow-Green 144A.

OTHER CHARACTERISTICS

Seeds and fruits: Seeds are minute and dark grey with a circular shape.

Disease/pest resistance: Neither resistance nor susceptibility observed. *Portulaca* is not typically susceptible to many diseases and pests. The most common diseases being typical root rots from over watering, or black stem, *Dichotomophthora portulaca*. The most common pest of *Portulaca* is Aphid.

Temperature tolerance: Will not tolerate temperatures below 7° C. High temperature tolerance near 40° C.

What is claimed is:

1. A new and distinct cultivar of *Portulaca* plant named 'DPORMPZGL' as herein illustrated and described.

* * * * *